United States Patent
Baurmeister

(10) Patent No.: US 6,918,886 B1
(45) Date of Patent: Jul. 19, 2005

(54) MEMBRANE MODULE FOR THE HEMODIAFILTRATION WITH INTEGRATED PRE- OR POSTDILUTION OF THE BLOOD

(75) Inventor: Ulrich Baurmeister, Wuppertal (DE)

(73) Assignee: Membrana GmbH, Wuppertal (DE)

( * ) Notice: Subject to any disclaimer, the term of this patent is extended or adjusted under 35 U.S.C. 154(b) by 541 days.

(21) Appl. No.: 10/089,943
(22) PCT Filed: Sep. 20, 2000
(86) PCT No.: PCT/EP00/09179

§ 371 (c)(1),
(2), (4) Date: Jul. 9, 2002

(87) PCT Pub. No.: WO01/24849
PCT Pub. Date: Apr. 12, 2001

(30) Foreign Application Priority Data

Oct. 6, 1999 (DE) .......................................... 199 47 901

(51) Int. Cl.⁷ ........................ A61M 37/00; B01D 61/00; B01D 63/02
(52) U.S. Cl. ........................ 604/6.09; 422/44; 210/646; 210/321.72; 210/321.79; 210/321.8; 210/321.81; 210/321.88; 210/321.89; 210/433.1; 210/500.23; 210/650
(58) Field of Search .............................. 604/4.01, 6.09; 422/44–48; 210/645–647, 650, 321.71–9, 500.21, 500.23, 433.1; 261/5, 6, 41.3, 49, 94, 97, 100, DIG. 28

(56) References Cited

U.S. PATENT DOCUMENTS

| | | | |
|---|---|---|---|
| 4,268,279 A | * | 5/1981 | Shindo et al. .................. 95/46 |
| 4,861,485 A | | 8/1989 | Fecondini |
| 5,660,722 A | | 8/1997 | Nederlof |
| 5,725,949 A | | 3/1998 | Pasquali et al. |
| 5,882,516 A | | 3/1999 | Gross et al. |
| 5,919,370 A | | 7/1999 | Röttger et al. |
| 5,964,725 A | * | 10/1999 | Sato et al. .................. 604/4.01 |
| 6,776,912 B2 | * | 8/2004 | Baurmeister ................. 210/646 |

FOREIGN PATENT DOCUMENTS

| | | | |
|---|---|---|---|
| DE | 28 51 929 | | 6/1980 |
| DE | 195 18 624 | | 11/1996 |
| DE | 196 07 162 | | 4/1998 |
| DE | 28 51 929 A1 | * | 1/2003 ............ A61M/1/03 |
| EP | 0 079 781 | | 11/1982 |
| EP | 0 451 429 A2 | | 10/1991 |
| EP | 0 692 269 | | 1/1996 |
| EP | 0 701 826 A2 | | 3/1996 |
| EP | 0 732 141 A1 | | 9/1996 |
| FR | 2 626 180 | | 7/1989 |
| JP | 10118472 | | 5/1998 |

OTHER PUBLICATIONS

B.L. Jaber et al., "New Polyether Sulfone Dialyzers Attenuate Passage of Cytokine–Inducing Substances from *Pseudomonas aeruginosa* Contaminated Dialysate," Blood Purification, 1998, vol. 16, pp. 210–219.

* cited by examiner

*Primary Examiner*—Angela D. Sykes
*Assistant Examiner*—Leslie R. Deak
(74) *Attorney, Agent, or Firm*—Oliff & Berridge, PLC

(57) ABSTRACT

A membrane module for hemodiafiltration having a cylinder-shaped housing and a bundle of hollow-fiber membranes capable of supporting fluid flow and arranged in the direction of the longitudinal extent of the housing. The ends of the hollow-fiber membranes are embedded in a fluid-tight manner in first and second sealing compounds joined to the housing inner wall in a fluid-tight manner. The exterior space formed around the hollow-fiber membranes and delimited by the first and second sealing compounds and the housing inner wall is divided along the longitudinal extent of the housing into a dialyzate space and a substituate space by a dividing wall that is made from a substantially dimensionally stable material. The dividing wall encloses each hollow-fiber membrane and is arranged substantially transversely to the hollow-fiber membranes. The dialyzate space and substituate space each have at least one opening for introducing or draining a fluid. In the exterior space, at least one throttle is arranged by which the dialyzate space and substituate space are in fluid communication with each other.

21 Claims, 9 Drawing Sheets

MEMBRANE MODULE FOR THE HEMODIAFILTRATION WITH INTEGRATED PRE- OR POSTDILUTION OF THE BLOOD

BACKGROUND OF THE INVENTION

1. Field of the Invention

The invention relates to a membrane module for hemodiafiltration, comprising a cylinder-shaped housing with a longitudinal extent housing a bundle of hollow-fiber membranes with semipermeable walls and capable of supporting fluid flow through their lumina arranged in the direction of the longitudinal extent of the housing. The ends of the hollow-fiber membranes are embedded in a fluid-tight manner in first and second sealing compounds joined to the housing inner wall in a fluid-tight manner such that an exterior space delimited by the first and second sealing compounds and the housing inner wall is formed around the hollow-fiber membranes. The exterior space along the longitudinal extent of the housing is divided into a dialyzate space and a substituate space by a dividing wall that is made from a substantially dimensionally stable material, encloses each hollow-fiber membrane, and is arranged substantially transversely to the hollow-fiber membranes, the dialyzate and substituate spaces each have at least one opening for introducing or withdrawing a fluid.

2. Discussion of Related Art

Hemodiafiltration is a combined membrane-based process for blood purification in which hemodialysis and hemofiltration are conducted concurrently. This process combines the advantages of convective substance transport in hemofiltration with those of diffusion in hemodialysis. In hemofiltration, blood is passed along the membrane of a hemofilter, a portion of the blood liquid being withdrawn through the membrane by ultrafiltration. This partial stream is replaced by a sterile and pyrogen-free substitution liquid, or substituate, that is delivered to the extracorporeal blood stream either upstream from the hemofilter in the form of predilution or downstream from the hemofilter in the form of post-dilution. In addition, in hemodiafiltration the usual hemodialysis is conducted as well, wherein a dialysis liquid or dialyzate is passed along the membrane of the hemodialyzer such that substances usually eliminated with the urine can be removed through the membrane.

The combination of diffusive substance transport with convective substance transport in hemodiafiltration permits the advantageous removal of more than only substances from the blood having a low molecular weight that are usually eliminated with the urine. Slowly diffusing medium molecules with molecular weights from about 1 to 55 kD profit especially from the convective substance transport, and that is all the more so as these molecules increase in size and as the filtrate stream through the membrane increases. Typically, at about 60 kD, the membranes are intended to be essentially impermeable, so that the patient does not pass more than 4 g of protein from the blood into the dialyzate during a 4-hour treatment.

In the conventional hemodialysis process, only the amount of liquid the patient has taken in between the dialysis treatments is removed from the blood via the dialysis membrane as ultrafiltrate. The amount of liquid removed in this process is about 6 to 8% of the blood volume stream. In conducting current hemodialysis processes, so-called volume-controlled dialysis machines are generally used. They monitor the net amount of liquid removed according to the preset net filtration by balancing the dialysis liquid stream fed to the dialyzer with the dialyzate stream withdrawn from the dialyzer, In hemodiafiltration, on the other hand, the amount of ultrafiltrate is significantly higher, from about 20 to 30% of the blood volume stream, due to the liquid fraction needed to increase the convective transport through the membrane. In the end, the net amount of liquid withdrawn from the patient is the same as that in conventional hemodialysis. The amount of liquid exceeding that needed to increase the convective transport is, as noted, replaced by a substituate.

To conduct hemodiafiltration processes, modified dialysis machines are generally used that permit monitoring of the ultrafiltration rates and balance the ultrafiltration and substituate volume streams.

Different requirements are usually imposed with respect to the purity of the dialysis and substitution liquids. The dialysis liquid can be prepared online from fresh water and an electrolyte concentrate, where the fresh water is normally germ-free and the electrolyte concentrate is inherently sterile. The substitution liquid itself can be prepared online from the dialysis liquid, but it is not generally required that the dialysis liquid prepared online is absolutely sterile and free of endotoxins, pyrogens and CIS.

Endotoxins are cell remnants of dead bacteria. The endotoxin concentration is usually determined using the so-called LAL test, a biological assay such as that manufactured by BioWhittaker, Inc., for example. Pyrogens are temperature-elevating substances. When infused in rabbits, for example, they cause an increase in body temperature. Pyrogens can include endotoxins and exotoxins. The latter are produced by living bacteria. In human blood, these substances lead to stimulation of monocytes that themselves produce cytokines and thus trigger a cascade of additional cell stimulations. Today, endotoxins, exotoxins, pyrogens, and other substances from the dialyzate that stimulate the blood are grouped under the abbreviation CIS (cytokine inducing substances). One of the relevant cytokines produced by stimulation of stimulated monocytes is interleukin 6 (IL 6). The determination of CIS by detection of IL 6 is described in B. L. Jaber et al., Blood Purif. 1998, Vol. 16, pp. 210–219, for example.

For this reason, the dialysis liquid for preparing the substitution liquid should be converted to the sterile and ideally CIS-free state, using a filter, for example. Of course, the substitution liquid prepared in this manner can also be used as a dialysis liquid. Modem dialysis machines generally include a facility with which the dialyzate is filtered online such that it has an endotoxin concentration of less than 0.5 EU per ml of dialyzate. As a result, patients experience almost no pyrogen reactions, even in the case of so-called high-flux dialysis, which are frequently observed with dialyzate contaminated with endotoxins. However, with an endotoxin concentration of <0.03 EU/ml, which is the detection limit of the conventional LAL tests, CIS might still be present in the dialyzate. The requirement for CIS-free dialyzate is therefore more stringent than that for LAL-negative dialyzate.

In EP-A 692 269, a hemodiafiltration apparatus is described with two blood filters connected in series. The blood filters each contain membranes, one side of which is subjected to a flow of blood to be purified and the other side to a dialysis liquid flow. The dialysis is passed through a sterile filter prior to being fed to the hemodiafiltration apparatus. In the apparatus described in EP-A 692 269, a transfer of dialysis liquid as a substitution liquid directly into the blood takes place in one of the two blood filters in the direction of the blood flow due to the positive transmembrane pressure set at this point via the membrane of this blood filter. A negative transmembrane pressure is generated in the second blood filter, where separation of a portion of the blood liquid and removal of substances normally eliminated in the urine into the dialyzate take place via diafiltration.

Such hemodiafiltration apparatus with blood filters connected in series are complex in operation and can generally not be used in commercially available dialysis machines due to the design and the special and complex controls associated with it.

EP-A 451 429 also discloses a hemodiafiltration apparatus having two membrane modules connected in series. In this case, the first membrane module is a hemofilter in which a partial stream of liquid is withdrawn by ultrafiltration from the blood to be purified, wherein the partial stream primarily contains the medium-molecular substances to be removed from the blood. The ultrafiltrate is regenerated in a special filter and reintroduced to the blood stream before the latter is directed into the second membrane module. This blood stream is then subjected to hemodialysis in the second membrane module.

In addition to the previously cited disadvantages of separate blood filters connected in series, the hemodiafiltration apparatus described in EP-A 451 429 has the drawback that it requires a special regenerator that must be used to purify the ultrafiltrate.

In DE-A 196 07 162, a hemodiafiltration system is described with controlled delivery of a substituate and a dialyzate into a dialyzer, wherein the dialyzer is designed as a single component for blood treatment, substituate filtering, and mixing of the substituate with the blood to be treated. The dialyzer contains two adjacent membrane modules in its longitudinally extended housing, each with a bundle of hollow-fiber membranes. The membrane modules are separated from each other by a dividing wall substantially parallel to the hollow-fiber membranes. The first membrane module is used for hemodiafiltration and the second membrane module for sterile filtration of the substituate. The dialyzer further comprises a chamber in which purified substituate is reunited with the blood to be treated.

While the hemodiafiltration system described in DE-A 196 07 162 has a simpler and clearer construction compared to the systems with multiple blood filters connected in series, the manufacture of the two-module dialyzers disclosed in DE-A 196 07 162 is difficult, particularly due in part to the handling of two different hollow-fiber membrane bundles. Furthermore, the membrane modules in the dialyzer are not arranged rotationally symmetrically, so that there is a risk of non-uniform flow, in particular through the external space surrounding the hollow-fiber membranes of the first membrane module, which is used for hemodiafiltration. Furthermore, the dialyzers as described in DE-A 196 07 162 also require an additional pump device for the substituate transport, which is not present in conventional dialysis machines today.

EP-A 701 826 discloses a hemodiafilter that has a single bundle of hollow-fiber membranes for blood treatment, filtration of the substituate, and delivery of the substituate to the blood. In this hemodiafilter, a material is present in the external space of the hemodiafilter surrounding the hollow-fiber membranes that undergoes dimensional changes, i.e., swells, through the dialysis liquid when this hemodiafilter is used for hemodiafiltration, leading to a restriction. This generates a pressure drop between the upstream and downstream sides of the restriction for the dialysis liquid flowing through the external space. Materials that can swell due to the dialysis liquid include, for example, various copolymers that are applied at the desired location on the hollow-fiber membranes, or fiber-shaped materials, capable of swelling, that are woven with the hollow-fiber membranes.

The insertion of the swellable material is complex, on one hand. On the other hand, a precise, stable, and reproducible positioning across the bundle cross-section is not guaranteed and cannot be achieved in practice. There are also narrow limits imposed on the materials capable of swelling that can be used since the use of the hemodiafilter for blood purification requires a high degree of hemocompatibility for the materials used, due to the contact with body liquids. Since, according to EP-A 701 826, the degree of swelling of the inserted swellable material depends on the dialysis liquid used, the degree of swelling is difficult to control and reproduce. The effect of the restriction caused by this material on the dialyzate and substituate flow cannot be determined in advance, or it requires at least comprehensive preliminary tests and complex estimations. Furthermore, due to the swelling there is a dependence of the material dimensions and thus the cross-section restriction on the differential pressure applied, and in an unfavorable case an increase in the pressure differential can lead to complete blockage.

From the previously described disadvantages, it can readily be concluded that controllable and reproducible flow conditions are not present when the hemodiafilters disclosed in EP-A 701 826 are used.

SUMMARY OF THE INVENTION

It is therefore an object of the present invention to provide a membrane module for hemodiafiltration that has a simple and compact construction, exhibits an improved ability to predetermine and reproduce the delivery of substituate and dialyzate, and can be used in volume-controlled dialysis machines without major modifications.

The object is achieved by a membrane module for hemodiafiltration comprising a cylinder-shaped housing with a longitudinal extent, housing a bundle of hollow-fiber membranes with semipermeable walls and capable of supporting fluid flow through their lumina, wherein the bundle of hallow-fiber members is arranged in the direction of the longitudinal extent of the housing. The ends of the hollow-fiber membranes are embedded in a fluid-tight manner in first and second sealing compounds joined to the housing inner wall in a fluid-tight manner such that an exterior space delimited by the first and second sealing compounds and the housing inner wall is formed around the hollow-fiber membranes. The exterior space along the longitudinal extent of the housing is divided into a dialyzate space and a substituate space by a dividing wall that is made from a substantially dimensionally stable material, encloses each hollow-fiber membrane, and is arranged substantially transversely to the hollow-fiber membranes, the dialyzate and substituate spaces each having at least one opening for introducing or draining a fluid, wherein at least one throttle is arranged in the exterior space by which the dialyzate spaces and substituate spaces are in fluid communication with each other.

DESCRIPTION OF PREFERRED EMBODIMENTS

Figure 1:
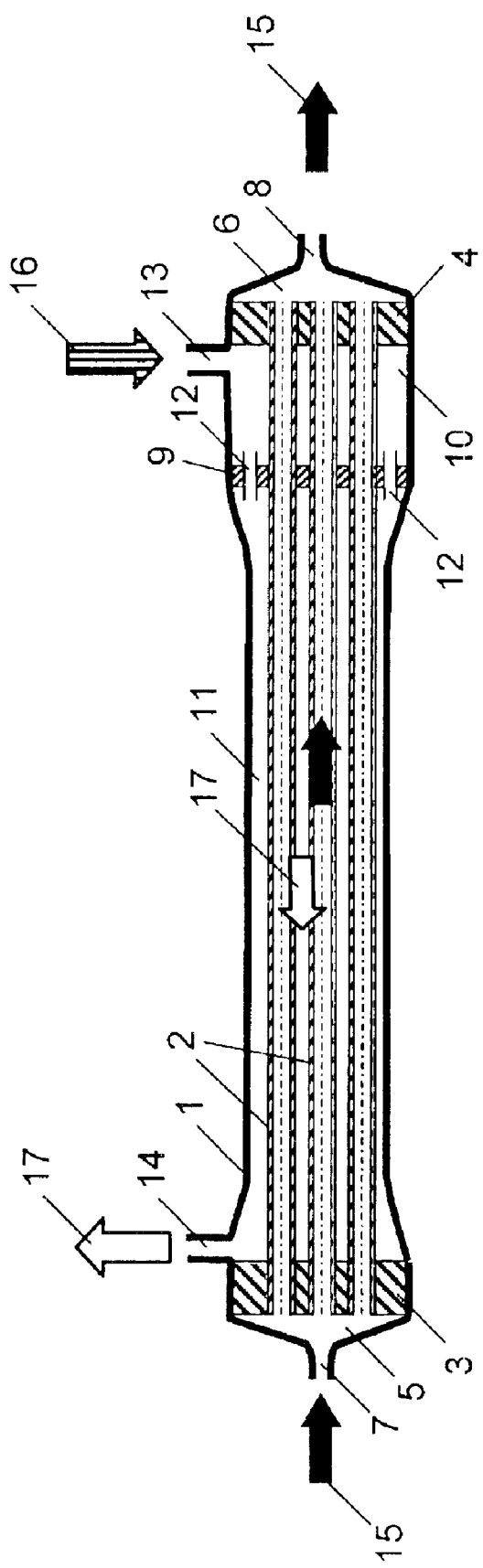
FIG. 1 shows a longitudinal section through a membrane module of the invention with throttles integrated into a dividing wall in the form of short capillaries arranged around the bundle of hollow-fiber membranes in a ring shape.

In the scope of the present invention, a throttle is understood to be a defined restriction of a flow cross-section to selectively generate a defined pressure drop when a fluid flows through this restriction. That is, the throttle exhibits a reduced flow cross-section compared to the flow cross-section before and after the throttle with respect to the direction of fluid flow. In this case, the flow cross-section of the throttle has a defined fixed value, independent of the passing fluid, or it can be adjusted to a defined value independent of the passing fluid. In such throttles, the pressure drop arising during flow can be predetermined. Throttles with a fixed cross-section, or adjustable to a fixed value include perforated or slit diaphragms and capillary tubes with defined diameters, for example. In a preferred embodiment of the membrane module of the invention, the throttle is adjustable.

In the scope of the present invention, a substantially dimensionally stable material is understood to be a material that, when used in the hemodiafiltration module of the invention, substantially retains its dimensions and shape under the then prevailing conditions compared to the original state of the module following its manufacture, and in particular does not swell in the presence of the liquids used in this case, i.e., primarily the dialysis liquid.

In a preferred embodiment of the membrane module of the invention, the housing is circularly cylindrical about its longitudinal axis oriented in the direction of the longitudinal extent, and the hollow-fiber membranes are arranged in a bundle that is substantially rotationally symmetrical about the longitudinal axis.

In the hemodiafilter of the invention, the ends of the hollow-fiber membranes are each embedded in sealing compounds that also seal off the exterior space formed around the hollow-fiber membranes with respect to a distribution space in which the blood to be treated is introduced into the collection space via a blood inlet arrangement and distributed to the lumina of the hollow-fiber membranes, and with respect to a collection space in which the blood flowing from the lumina is collected and drained from the module via a blood outlet arrangement. The ends, open on the face, of the hollow-fiber membranes extend through the respective sealing compound and are in communication with the distribution and collection spaces via the lumina, so that the blood to be treated can pass through the membranes.

Due to the fact that in the hemodiafilter of the invention, the same hollow-fiber membranes are used for blood treatment, filtering of the substituate, and delivery of the substituate to the blood, and that the dialyzate and substituate spaces are separated from each other by a dividing wall, the dialyzate and substituate spaces are arranged adjacent to each other at different positions along the hollow-fiber membranes when viewed in the direction of the extent of the hollow-fiber membranes with the dividing wall at least substantially filling out the inner cross-section of the housing. In the membrane module of the invention, at least one throttle is arranged in the exterior space in accordance with the invention, by which the substituate and dialyzate spaces are in fluid communication with each other. It follows from this that the at least one throttle is arranged in the dividing wall or in the area thereof, i.e., integrated into the dividing wall or encircling the dividing wall in the exterior space within the housing.

In a preferred embodiment, the membrane module of the invention has only one opening in the substituate space area which serves as an inlet arrangement for introducing the dialysis liquid into the substituate space, and only one opening in the dialyzate space area which serves as an outlet arrangement for draining the dialyzate from the dialyzate space. This is particularly advantageous in the interest of compatibility with connections to modern dialysis machines.

During use of the hemodiafilter of the invention, the blood to be purified is directed through the lumina of the hollow-fiber membranes. By suitable delivery means, e.g., a pump, a stream of dialysis liquid is supplied to the hemodiafilter and introduced under increased pressure into the substituate space via the opening of the substituate space serving as the inlet arrangement for the dialysis liquid, i.e., via the inlet arrangement of the substituate space. A portion of the dialysis liquid introduced into the substituate space is delivered as a substituate with a defined volume stream to the blood flowing through the lumina of the hollow-fiber membranes, via the walls of the portions of the hollow-fiber membranes located in the substituate space. The substituate volume stream is influenced largely by the increased pressure and the permeability of the hollow-fiber membranes. The amount of substituate introduced per time unit, i.e., the substituate volume stream, is the difference between the liquid stream withdrawn from the blood in the dialyzate space area via ultrafiltration and the net filtration controlled and fixedly preset by the dialysis machine.

By the at least one throttle arranged in the exterior space of the invention, the major portion of the total dialysis liquid delivered to the hemodiafilter is directed as dialyzate with a defined volume stream into and flows through the dialyzate space. The volume stream of the dialyzate introduced into the dialyzate space, and thus the ratio of the dialyzate volume stream to the substituate volume stream depends substantially on the number of throttles and the flow resistance generated by them compared to the flow resistance that must be overcome by the substitute stream when permeating the walls of the hollow-fiber membranes.

In the dialyzate space, the dialyzate is passed along the hollow-fiber membranes, thereby also taking up the ultrafiltrate withdrawn from the blood via ultrafiltration through the walls of the hollow-fiber membranes, so that the substances normally eliminated in the urine are removed from the blood via convective and diffusive transport mechanisms. The dialyzate, mixed with the ultrafiltrate, is withdrawn from the dialyzate space via the opening of the dialyzate space serving as the outlet arrangement for the dialyzate, i.e., via the outlet arrangement of the dialyzate space. Depending on the direction of blood flow through the hollow-fiber membranes, the substitute can be delivered to the blood before it is subjected to hemodiafiltration (pre-dilution) or after it has been subjected to hemodiafiltration (post-dilution). The membrane module of the invention is thus designed such that hemodiafiltration with integrated pre- or post-dilution of the blood can be conducted.

Through the design of the membrane module of the invention for hemodiafiltration, i.e., the hemodiafilter of the invention, it is possible, in a simple, controllable, and reproducible manner, to integrate the dilution of the blood with substituate, as required in hemodiafiltration, and the hemodiafiltration in a single membrane module, which like conventional hemodialyzers contains only one bundle of hollow-fiber membranes, so that the hemodiafiltration in commercially available dialysis machines can be conducted with ultrafiltration in which the volume stream is controlled. At the same time, the separation of the substituate and dialyzate spaces via the dividing wall of the invention, which is substantially dimensionally stable and is not substantially swellable in the dialysis liquid, in conjunction with the at least one throttle of the invention, via which the dialyzate and substituate spaces are in fluid communication with each other, ensures the adjustment of a volume stream ratio between the substituate and dialyzate that can readily be predetermined and reproduced.

Compared to known hemodiafilters, such as those described in DE-A 196 07 162 or EP-A 701 826, the hemodiafilter of the invention, with a dividing wall in which, or in the area of which, at least one throttle is arranged, offers the advantage of a very compact construction with only one hollow-fiber membrane bundle, which is used for blood treatment, filtering of the substituate, and delivery of the substituate to the blood, with the throttle providing a means for reliable and precise adjustment of the pressure and pressure-drop conditions, resulting in defined volume streams of dialyzate and substituate.

DE-A 28 51 929 discloses a module design on the basis of hollow-fiber membranes, wherein the dialyzate space is divided into two sections by an impermeable dividing wall. In one embodiment, dialyzate is directed through the one section which is provided with an inlet arrangement and an outlet arrangement in order to remove, by diffusion, substances normally eliminated in the urine from the blood flowing through the hollow-fiber membranes. The second section, which is provided with an outlet arrangement, is subjected to a partial vacuum in order to extract, via the walls of the hollow-fiber membranes, a filtrate from the blood flowing through them. In DE-A 28 51 929, the dividing wall seals off the two sections of the module from each other in a fluid-tight manner and does not contain a throttle by which dialysis liquid might be passed from one subspace into the other. This module is therefore not suitable for use in hemodiafiltration.

In the hemodiafiltration system of the invention, the delivery of the substituate to the blood can take place before or after the blood is subjected to diafiltration in the dialyzate space area In an individual case, it is also possible to divide the substituate space, and thus the delivery of the substituate to the blood, along the extent of the hollow-fiber membranes and deliver one part of the substituate to the blood before and one part after the diafiltration. In this case, in the hemodiafilter of the invention, two substituate-space sections are arranged along the extent of the hollow-fiber membranes adjacent to the embedding point of the hollow-fiber membrane ends, each section being separated by a dividing wall from an intermediate dialyzate space, at least one throttle being arranged in or in the area of at least one of the dividing walls. In a corresponding manner, it is also possible to divide the dialyzate space, and thereby the diafiltration, and to arrange two dialyzate-space sections along the extent of the hollow-fiber membranes adjacent to the embedding point of the hollow-fiber membrane ends, each section being separated by a dividing wall from an intermediate substituate space. In these cases, at least one throttle is arranged in or in the area of each of the dividing walls.

In a preferred embodiment of the membrane module of the invention, the dividing wall is joined to the housing inner wall in a fluid-tight manner and the at least one throttle arranged in the exterior space is integrated into the dividing wall so that the dividing wall is permeable for the dialysis liquid via the at least one throttle and a portion of the dialysis liquid can be directed as dialyzate from the substituate space into the dialyzate space.

In the most basic embodiment, the at least one throttle integrated into the dividing wall is at least one hole with a defined diameter, generally a plurality of holes, which are preferably arranged in a ring around the hollow-fiber membrane bundle. The inlet arrangement of the substituate space and outlet arrangement of the dialyzate space are, for practical reasons, arranged at the ends of the respective spaces facing away from the dividing wall.

Preferably, the at least one throttle integrated into the dividing wall is at least one capillary inserted into the dividing wall, via the lumen of which the dialyzate and substituate spaces are in fluid communication with each other. More preferably, a plurality of capillaries is arranged around the bundle of hollow-fiber membranes, a particularly preferred embodiment is a ring-shaped arrangement, such as the form of a circular ring in the case of a bundle with a substantially circular cross-section.

Based on the diameter of the lumina of the capillaries, the number of capillaries, and their length, and using simple fluid-mechanics calculations, the throttle action can be determined and thereby the ratio of dialyzate and substituate volume streams predetermined and accordingly preset.

With respect to the capillary length, two preferred embodiments can be distinguished. When using short capillaries, it is practical in the interest of problem-free insertion of such capillaries into the dividing wall for the capillary length to exceed the thickness of the dividing wall. However, in the interest of uniform flow through the dialyzate space, the capillaries should extend into it only a short distance. Preferably, the length of the capillaries exceeds the thickness of the dividing wall by less than 100%. For these cases, the inlet arrangement of the substituate space and outlet arrangement of the dialyzate space are, for practical reasons, arranged at the ends of the respective spaces facing away from the dividing wall.

In another preferred embodiment, at least one long capillary extends through the dialyzate space and terminates in the area before the sealing compound delimiting the dialyzate space. In this case, the outlet arrangement of the dialyzate space is then arranged adjacent to the dividing wall. This embodiment of the membrane module of the invention can be preferably used for blood purification in which a predilution of the blood with substitute takes place, before the blood is subjected to diafiltration. The blood then flows at the side of the housing into the hemodiafilter, which faces the substituate space and exits the housing at the opposite end, which faces the dialyzate space. On its path through the hollow-fiber membranes, the blood is first diluted with substituate and then subjected to hemodiafiltration in the dialyzate space area, wherein due to the extension through the dialyzate space of the at least one long capillary used as a throttle and the arrangement of the dialyzate space opening in the vicinity of the dividing wall, the dialyzate is passed along the outside of the hollow-fiber membranes in the direction opposite to the direction of blood flow. Multiple capillaries used in this embodiment can also be combined with hollow-fiber membranes, for example, and embedded together with them at one end in the dividing wall. In this case, the dividing wall is constructed from a sealing compound. This results in uniform dialyzate distribution during use.

In an especially preferred embodiment, a single long capillary extending through the dialyzate space is inserted into the dividing wall, the capillary arranged centrally in the bundle of hollow-fiber membranes and by which the dialyzate and substituate spaces are in fluid communication with each other. To achieve the required throughput of dialysis liquid through this capillary, which functions as a throttle, the capillary can also have a relatively large diameter. It is also possible for the diameter of the capillary to be more that of a tube, i.e., for the capillary to be a tube, in which case the desired throttle action of this tube can be generated by selective restrictions in the inside of the tube, for example. Preferably, such tubes can serve as winding cores at the same time when the hollow-fiber membranes are arranged adjacent and parallel to one another in mats and the hollow-fiber membrane bundle is produced, for example, by spirally winding at least one hollow-fiber membrane mat around the tube with the hollow-fiber membranes arranged parallel to the tube axis. In this case, the tube can also extend over the entire length between the first and second sealing compounds and be embedded in them such that the tube's interior is separated from the distribution and collection spaces in a fluid-tight manner. In this case, the tube in the area of the substituate and dialyzate spaces has openings in its wall, via which dialysis liquid can enter in the substituate space area and dialyzate can exit in the dialyzate space area The openings can at the same time function as throttles.

In another preferred embodiment of the membrane module of the invention, the at least one throttle is at least one semipermeable, preferably consistently microporous capillary membrane embedded in the dividing wall, the lumen of which is open at one end and closed at the other. This at least one capillary membrane is preferably embedded in the dividing wall such that the closed end extends into the substituate space and the open end opens or extends into the dialyzate space. In hemodiafiltration, dialyzate liquid then flows in the substituate space area in so-called dead-end mode into the lumen of the at least one capillary membrane via its semipermeable wall and exits via the open end of the capillary membrane into the dialyzate space. The throttle action of the at least one capillary membrane results from the pressure drop arising during the flow through the porous, semipermeable wall of the capillary membrane.

In a likewise preferred embodiment of the membrane module of the invention, a plurality of throttles in the form of annular-gap segments are arranged in the dividing wall around the bundle of hollow-fiber membranes or on the periphery of the dividing wall.

According to another preferred embodiment of the membrane module of the invention, the at least one throttle arranged in the exterior space is an annular gap formed around the bundle of hollow-fiber membranes between the dividing wall and housing inner wall. In this case, the dividing wall is, of course, not joined to the housing inner wall in a fluid-tight manner. To fix the dividing wall and stabilize the spacing, it is practical to insert spacers between the dividing wall and housing inner wall such that provision is made for a defined stable annular gap and thereby a defined throttle action.

It is preferred for the dividing wall, together with the hollow-fiber membrane bundle, to be embedded at its periphery in a sleeve in a fluid-tight manner. This sleeve then has a defined spacing from the housing inner wall, forming an annular gap representing the throttle. By using a sleeve, considerable influence can be exerted, by not only the gap width but also by the length of the sleeve, on the pressure drop generated by the gap and thus on the throttle action. The required length of the annular gap formed in the dividing wall area between the sleeve and housing inner wall along the longitudinal extent of the housing then results, together with the annular-gap width, from the desired throttle action of the annular gap. In another preferred embodiment, the dividing wall is embedded in a fluid-tight manner along its periphery, together with the hollow-fiber membrane bundle, in a sleeve whose outside diameter is substantially the same as the inside diameter of the housing, but where grooves extending in the axial direction of the housing are provided in the outside of the sleeve and/or in the housing inner wall. The sleeve is then pressed substantially tightly into the housing such that the grooves represent a plurality of defined throttles.

The hollow-fiber membrane bundle in such embodiments can also be inserted into a sleeve over its entire end region facing the dividing wall or also over its entire extent. In this case as well, the dividing wall is joined to the sleeve in a fluid-tight manner. To ensure a good distribution of the fluid over the hollow-fiber membrane bundle, the sleeve in the area of the fluid inlets or outlets is then provided with openings, for example, in the form of holes, and, for practical reasons, shaped such that a wider gap is formed there between the housing and sleeve than in the dividing wall area. In the dialyzate space area, the outside of the sleeve is tightly adjacent to the housing inner wall, with no gap.

By constructing the sleeve and housing inner wall in the dividing wall area in the form of wedges, whose inclined surfaces face each other when viewed in the longitudinal section of the membrane module, an annular gap can be formed whose width is preferably adjustable. Different gap widths can be formed by modifying the position of the wedges with respect to each other. The annular gap in this case can be adjusted by modifying the position of the membrane bundle along the longitudinal extent of the housing or by a wedge that can be displaced within the housing wall.

Also, in the previously described embodiment in which the at least one throttle is in the form of annular gaps, segments thereof, or grooves, it is practical to position the inlet arrangement of the substituate space and the outlet arrangement of the dialyzate space at the ends of the respective spaces facing away from the dividing wall. In these embodiments of the membrane module of the invention, as well as in embodiments in which the throttles are in the form of holes in the dividing wall or short capillaries, the respective membrane modules are used for hemodiafiltration processes in which a post-dilution of the blood with substituate takes place. That is, the necessary liquid is first withdrawn from the blood in the dialyzate space area by ultrafiltration and then substituate delivered to the blood in the substituate space area. To this end, the blood flows into the hollow-fiber membranes at the end of the hemodiafilter facing away from the substituate space and through the membranes in the direction of the end facing toward the substituate space. The dialyzate then flows through the dialyzate space in a direction opposite that of the blood flow.

In conducting hemodiafiltration, an external sterile filter is often connected upstream from the hemodiafilter itself, providing sterile filtration of the dialysis liquid or at least the liquid delivered as a substituate. In a preferred embodiment of the membrane module of the invention, a sterile filter is arranged within the membrane module around the hollow-fiber bundle in the substituate space area, wherein the filter encloses the hollow-fiber membrane bundle. This sterile filter divides the substituate space perpendicularly to the extent of the hollow-fiber membranes into outer and inner substituate-space sections. A pleated flat membrane can be used as a sterile filter in one preferred embodiment. It is preferred to use a flat membrane that is consistently microporous. The sterile filter is preferably impermeable to endotoxins and more preferably impermeable to CIS, thereby ensuring during use the delivery of a sterile substituate to the hollow-fiber membranes that is free of endotoxins and pyrogens and preferably free of CIS. In this case, a sterile filter impermeable to endotoxins is understood to be one for which, in filtering a contaminated dialysis liquid with an endotoxin concentration of up to 30 EU/ml at a filtration rate of 150 ml/min over 4 hours through the sterile filter, the filtrate has an endotoxin concentration below the detection limit of conventional tests, i.e., below about 0.03 EU/ml. The endotoxin concentration is determined using conventional LAL tests such as those sold and described by BioWhittaker, Inc. (MULTI-TEST LIMULUS AMEBOCYTE LYSATE PYROGENT®).

The sterile filter in this embodiment can be arranged such that, during use, the entire dialysis liquid delivered to the hemodiafilter of the invention is filtered by the sterile filter. In this embodiment, only a distribution of the dialysis liquid over the entire surface of the sterile filter takes place in the outer section of the substituate space, and the at least one throttle, by which the substituate space and dialyzate space are in fluid communication, is integrated into the dividing wall in the area of the inner section of the substituate space.

Generally, however, a sterile filtration of the entire dialysis liquid is unnecessary since the portion of the dialysis liquid passed as dialyzate along the hollow-fiber membranes is not subject to the stringent purity requirements applying to the substituate. Preferably, the sterile filter is therefore arranged in the membrane module of the invention such that during use only the portion flows through the sterile filter that is finally delivered as substituate to the blood flowing through the hollow-fiber membranes. This is achieved by arranging the at least one throttle in the area of the outer section of the substituate space and having only the outer section of the substituate space in fluid communication with the dialyzate space. The inner section of the substituate space, on the other hand, is separated from the dialyzate space in a fluid-tight manner. As previously noted, the throttle in this case can, for example, be in the form of capillaries integrated into the dividing wall or an annular gap formed between the dividing wall and housing inner wall.

In individual cases, it is also possible to embed additional semipermeable membrane elements in the sealing compound adjacent to the substituate space, in which the hollow-fiber membrane ends are embedded, in order to increase the substituate stream to be delivered to the blood. The flow through these membrane elements is then performed in dead-end mode, and they provide fluid communication between the substituate space and the space on the other side of the sealing compound, wherein this space is the distribution or collection space for the blood depending on the embodiment of the membrane module of the invention. A further portion of the dialysis liquid can be delivered by these membrane elements, which also function as throttles, as substituate to the blood then located in the adjacent collection or distribution spaces. These semipermeable membrane elements can be present, for example, in the form of capillary membranes that are closed at one end, are preferably consistently microporous, are embedded in the sealing compound, and extend into the substituate space at their closed end. These membrane elements are, like the aforementioned sterile filter, preferably impermeable to endotoxins and more preferably impermeable to CIS. Refer to the preceding discussion regarding the definition of endotoxin and CIS impermeability and the respective measurement methods.

A maximally uniform distribution of substituate and dialyzate over the bundle cross-section is necessary in the use of the membrane module of the invention. A uniform distribution can be achieved by an appropriate housing design. Preferably, the housing of the membrane module of the invention is designed such that it tightly encloses the bundle of hollow-fiber membranes in the predominant portion of the dialyzate space with its inside closely fitting and exhibits an expansion of its cross-section in the area of the dividing wall and substituate space and possibly the scaling compounds. Thus, in a preferred embodiment, ring-shaped spaces are formed around the bundle of hollow-fiber membranes in these areas in order to distribute the dialysis liquid and dialyzate to the hollow -fiber membrane bundle or collect the dialyzate from the membrane bundle.

Preferably, the bundle has, at least in the predominant portion of the dialyzate space, a packing density of the hollow-fiber membranes between 40 and 65%, in reference to the bundle cross-sectional area and substantially uniform in this area over the extent of the bundle. It has been observed that, for the hemodiafilter used in accordance with the invention, i.e., the membrane module of the invention, such packing densities allow good removal of the substances normally eliminated via the urine from the blood.

In a likewise preferred embodiment, the housing is designed such that it encloses the bundle of hollow-fiber membranes in the dialyzate space area with its inside closely fitting and in the area of the scaling compounds, dividing wall, and substituate space, exhibits an expansion of the housing cross-section. The hollow-fiber membrane bundle is arranged in the housing such that the cross-section of the hollow-fiber membrane bundle expands in the area of the dividing wall and substituate space, and the packing density of the hollow-fiber membranes in this area is thereby less than in the predominant portion of the dialyzate space. As a result, the hollow-fiber membranes in the interior of the bundle are also easily accessible to the dialysis liquid and substituate, and the substituate flows uniformly into all hollow-fiber membranes of the bundle. In its expanded portion, the bundle preferably has a packing density between 20 and 55%, in reference to the respective bundle cross-sectional area, In such embodiments, it is especially preferable for the at least one throttle to be in the form of several capillaries arranged in a ring shape around the bundle of hollow-fiber membranes or in t he form of an annular gap between the dividing wall and housing inner wall.

The dividing wall of the hemodiafilter or membrane module of the invention preferably is composed of a scaling compound in which the hollow-fiber membranes are embedded such that it encloses each hollow-fiber membrane in order to simplify the manufacturing. It is especially preferable for the dividing wall and first and second scaling compounds to be made of the same material. In this case, the materials commonly used as sealing compounds for embedding hollow-fiber membranes, such as polyurethane resins, epoxy resins, and the like can be used.

To conduct an efficient hemodiafiltration, it is necessary that a sufficiently large exchange surface area be available for diafiltration in order to efficiently remove the substances normally eliminated in the urine from the blood. However, a sufficient membrane surface area must be available as well in order to permit reliable delivery of the required amount of substituate to the blood. For this reason, viewed in the direction of the extent of the hollow-fiber membranes, the ratio $L_d/L_s$, wherein $L_d$ is the length of the dialyzate space and $L_s$ is the length of the substituate space, is preferably between 3 and 20, and especially preferably between 5 and 15 for the hemodiafilter of the invention.

To likewise provide as large a membrane surface area as possible for substituate delivery to the blood and for hemodiafiltration, the dividing wall in the membrane module of the invention should be as thin as possible. However, a certain minimum thickness is necessary to ensure sufficient stability of the dividing wall. It is therefore preferred for the dividing wall to have a thickness between 1 and 15 mm, and especially preferred to have a thickness between 5 and 10 mm.

For efficient hemodiafiltration, it is necessary to generate a sufficiently high convective transport in order to remove the slowly-diffusing substances normally eliminated with the urine, in particular the substances having medium molecular weight. Moreover, it is preferred if only a relatively small section of the hollow-fiber membrane bundle is needed for the delivery of substituate to the blood. This means that a sufficiently high filtrate flow through the membrane wall must be realizable. For this reason, the hollow-fiber membranes present in the membrane module of the invention have an ultrafiltration rate for water between 20 and 1500 ml/(h·m$^2$·mmHg). The ultrafiltration rate in this case is determined using the method described in DE-A 195 18 624, and reference is hereby made to its disclosure in this regard.

For the reliable operation of the membrane module of the invention, it is important that no undesired contamination of the blood flowing through the hollow-fiber membranes with bacteria, endotoxins, or pyrogens occurs, in particular when delivering the substituate to the blood. As previously discussed, the dialysis liquid, or at least the substituate can, to this end, be subjected to a sterile filtration in a separate sterile filter or one integrated in the membrane module of the invention. Alternatively or in addition, this sterile filtration, however, can also take place in the hollow-fiber membranes themselves of the membrane module of the invention. Therefore, in a preferred embodiment of the membrane module of the invention, the hollow-fiber membranes are impermeable to endotoxins and especially preferably impermeable to cytokine-inducing substances. The impermeability in this case can be achieved by an appropriately adjusted pore size of the functional separation layer of the membranes and/or by adsorptive properties of the hollow-fiber membranes. Refer to the preceding discussion regarding the definition of endotoxin and CIS impermeability and the respective measurement methods.

The hollow-fiber membranes of the invention used preferably have an inside diameter between 140 and 260 μm, with a wall thickness preferably between 5 and 100 μm, and more preferably between 20 and 60 μm. Membrane materials are preferably those having good blood compatibility. These include polymers from the group of cellulosic polymers such as cellulose or regenerated cellulose, modified cellulose such as cellulose esters, cellulose ethers, amine-modified celluloses, and mixtures of cellulosic polymers from the group of synthetic polymers such as polyacrylonitrile and corresponding copolymers, polyarylsulfones, and polyarylethersulfones such as polysulfone or polyethersulfone, polyamides, polyether block amides, polycarbonates, or polyesters, as well as modifications, blends, mixtures, or copolymers derived from these polymers. These polymers or polymer mixtures can contain additional polymers such as polyethylene oxide, polyhydroxyether, polyethylene glycol, polyvinylpyrrolidone, polyvinyl alcohol, or polycaprolactone as additives. In an individual case, the membrane can for example also have been subjected to a surface modification in order to give certain properties to the membrane surface, for example in the form of certain functional groups, or to achieve the hydrophilation of an otherwise hydrophobic membrane on its surfaces, as is described for example in JP-A 10118472.

No restrictions are placed on the construction of the bundle of hollow-fiber membranes arranged in the membrane module of the invention, i.e., the arrangement of the hollow-fiber membranes in the bundle. A good flow around the individual hollow-fiber membranes should be ensured, however. In a preferred construction, the hollow-fiber membranes are substantially parallel to each other and to the longitudinal axis of the bundle, and the spacing between them is maintained by textile threads. This can be achieved, for example, before the bundle is assembled by weaving the hollow-fiber membranes to form a mat or ribbon of parallel hollow-fiber membranes and then configuring them to form a bundle. The bundle contained in the membrane module of the invention can also be composed of bundle sections as long as during use each of the hollow-fiber membranes of the bundle contributes to blood treatment, filtration of the substituate, and delivery of the substituate to the blood. Such a construction of bundle sections, in which the sections are wrapped with threads to improve the flow around the hollow-fiber membranes and the hollow-fiber membranes within the sections are spaced using support threads, is described in EP-A 732 141, for example. Moreover, the hollow-fiber membranes can also exhibit an undulation.

The invention will now be explained in more detail with reference to the figures, which are simplified schematic representations:

FIG. 1 shows a membrane module of the invention that can be used in hemodiafiltration procedures in which a post-dilution of the blood with substituate takes place. The membrane module according to FIG. 1 has a cylinder-shaped housing 1 in which a bundle of hollow-fiber membranes 2 is arranged, wherein the membranes are oriented in the direction of the longitudinal extent of the housing. The ends of the hollow-fiber membranes are embedded in a fluid-tight manner in sealing compounds 3 and 4, which are themselves joined to the inner wall of housing 1 in a fluid-tight manner. The hollow-fiber membranes are embedded in sealing compounds 3 and 4 such that their ends extend through the sealing compounds 3 and 4 and their lumina open into the distribution space 5 and collection space 6. The distribution space 5 has a blood inlet arrangement 7 and the collection space 6 a blood outlet arrangement 8.

Encircling the hollow-fiber membranes 2 between sealing compounds 3 and 4 and the inner wall of housing 1 is an exterior space that is divided into a substituate space 10 and a dialyzate space 11 along the extent of the hollow-fiber membranes 2 by a dividing wall 9 running transversely to the hollow-fiber membranes 2 that is substantially dimensionally stable and made, for example, of an epoxy or polyurethane sealing compound. The dividing wall 9 encloses the individual hollow-fiber membranes 2 and, in the case shown in FIG. 1, is joined in a fluid-tight manner to the housing inner wall. Short capillaries 12 are embedded into the dividing wall 9 as throttles and arranged in a ring shape around the bundle of hollow-fiber membranes 2. The substituate space 10 and dialyzate space 11 are in fluid communication with each other via capillaries 12. In order to be able to arrange the capillaries 12 in a ring shape around the hollow-fiber membrane bundle and achieve good distribution of the dialysis liquid in the substituate space 10 during use, the housing 1 of the membrane module shown in FIG. 1 has an expanded cross-section in the area of dividing wall 9 and substituate space 10. The substituate space has only an inlet arrangement 13 for the dialysis liquid, and the dialyzate space only an outlet arrangement 14 for the dialyzate. In the area of outlet arrangement 14, the cross-section of the housing 1 is also expanded in order to withdraw the dialyzate uniformly from the module.

During use, the blood, indicated by arrows 15, flows via the blood inlet arrangement 7 into the distribution space 5, through the lumina of the hollow-fiber membranes 2, then out of the hollow-fiber membranes 2 into the collection space 6, and is conducted out of the membrane module or hemodiafilter via the blood outlet arrangement 8. The dialysis liquid, indicated by arrow 16, is introduced into the substituate space 10 via inlet arrangement 13. A portion of the dialysis liquid flows in the area of substituate space 10 as a substituate into the hollow-fiber membranes 2 leading through it and mixes with the blood flowing through the hollow-fiber membranes 2. The major portion of the dialysis liquid flows via the throttles in the form of capillaries 12 as dialyzate 17 into the dialyzate space 11 and flows through the dialyzate space 11 in a direction opposite to that of the blood flow. In this process, the dialyzate 17 takes up the ultrafiltrate flowing out through the walls of the hollow-fiber membranes 2, together with the substances removed from the blood that are normally eliminated in the urine. The dialyzate 17, mixed with the ultrafiltrate, is withdrawn from the dialyzate space 11 via the outlet arrangement 14. In the module depicted in FIG. 1, the ultrafiltrate is initially withdrawn from the blood and the substituate is then delivered to it. A post-dilution of the blood therefore takes place.

Figure 2:
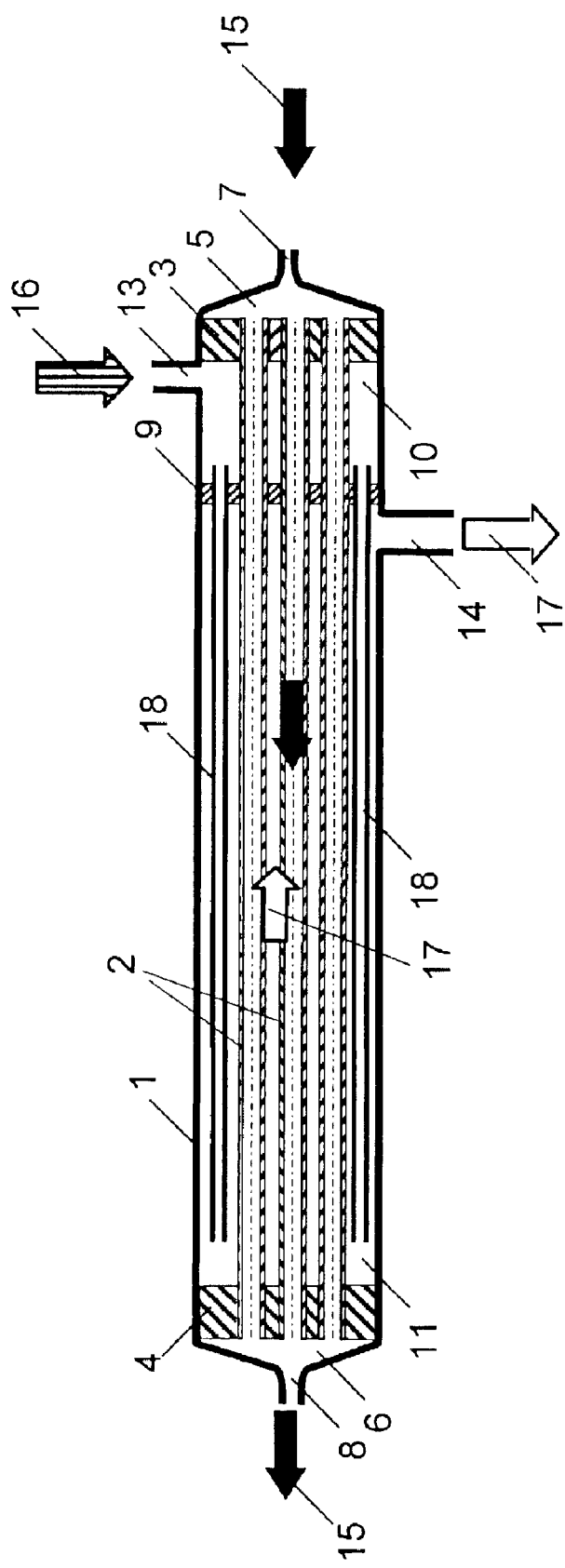
FIG. 2 shows a longitudinal section through a membrane module of the invention with throttles integrated in to a dividing wall in the form of long capillaries that are arranged around the bundle of hollow-fiber membranes in a ring shape.

The membrane module of the invention shown in FIG. 2 is suited to hemodiafiltration procedures in which a pre-dilution of the blood takes place. To a substantial extent, the membrane module according to FIG. 2 corresponds to that in FIG. 1, so that the same components are designated with the same reference numbers and a detailed description is not repeated. In contrast to the membrane module of FIG. 1, however, long capillaries 18 are embedded in the dividing wall 9 of the membrane module of FIG. 2 as throttles, in a ring shape around the bundle of hollow-fiber membranes 2 in housing 1 of this module. These capillaries 18 extend through the dialyzate space 11 to a point shortly before the sealing compound 4 facing the blood outlet arrangement 8. Such long capillaries 18 can be advantageously bound in parallel to form a mat, which can then be wrapped around the hollow-fiber membrane bundle in a simple manner. Thereafter, the capillaries can be embedded with the hollow-fiber membranes in the dividing wall.

During hemodiafiltration, the blood is directed via blood inlet arrangement 7 and distribution space 5 into, and flows through, the hollow-fiber membranes 2. In this process, substituate is delivered to the blood in the area of substituate space 10 and the blood thereby diluted with substituate before it passes, on its way through the hollow-fiber membranes 2, through the area of dialyzate space 11, in which the required liquid is withdrawn from the blood by ultrafiltration through the walls of the hollow-fiber membranes and the substances normally eliminated in the urine removed in the process. The purified blood, adjusted to the required liquid content, leaves the membrane module of the invention via the blood outlet arrangement 8.

The dialysis liquid 16 is introduced via the inlet arrangement 13 into the substituate space 10, which in the module embodiment according to FIG. 2 is arranged at the ends of the hollow-fiber membranes 2 facing the blood inlet arrangement 7. In the substituate space 10, a portion of the dialysis liquid flows as a substituate through the walls of the hollow-fiber membranes 2 into the blood flowing through the hollow-fiber membranes and dilutes it. The major portion of the dialysis liquid flows into the dialyzate space as dialyzate 17 through long capillaries 18 embedded as throttles in the dividing wall 9. The dialyzate 17 leaves the capillaries in the vicinity of the sealing compound 4 facing blood outlet arrangement 8 and flows through the dialyzate space in a direction opposite to that of the blood flow in the direction of the dividing wall 9. In this process, it takes up the ultrafiltrate with the substances removed from the blood that are normally eliminated with the urine and is withdrawn from the dialyzate space 11 via the outlet arrangement 14 located in the vicinity of the dividing wall 9.

Figure 3:
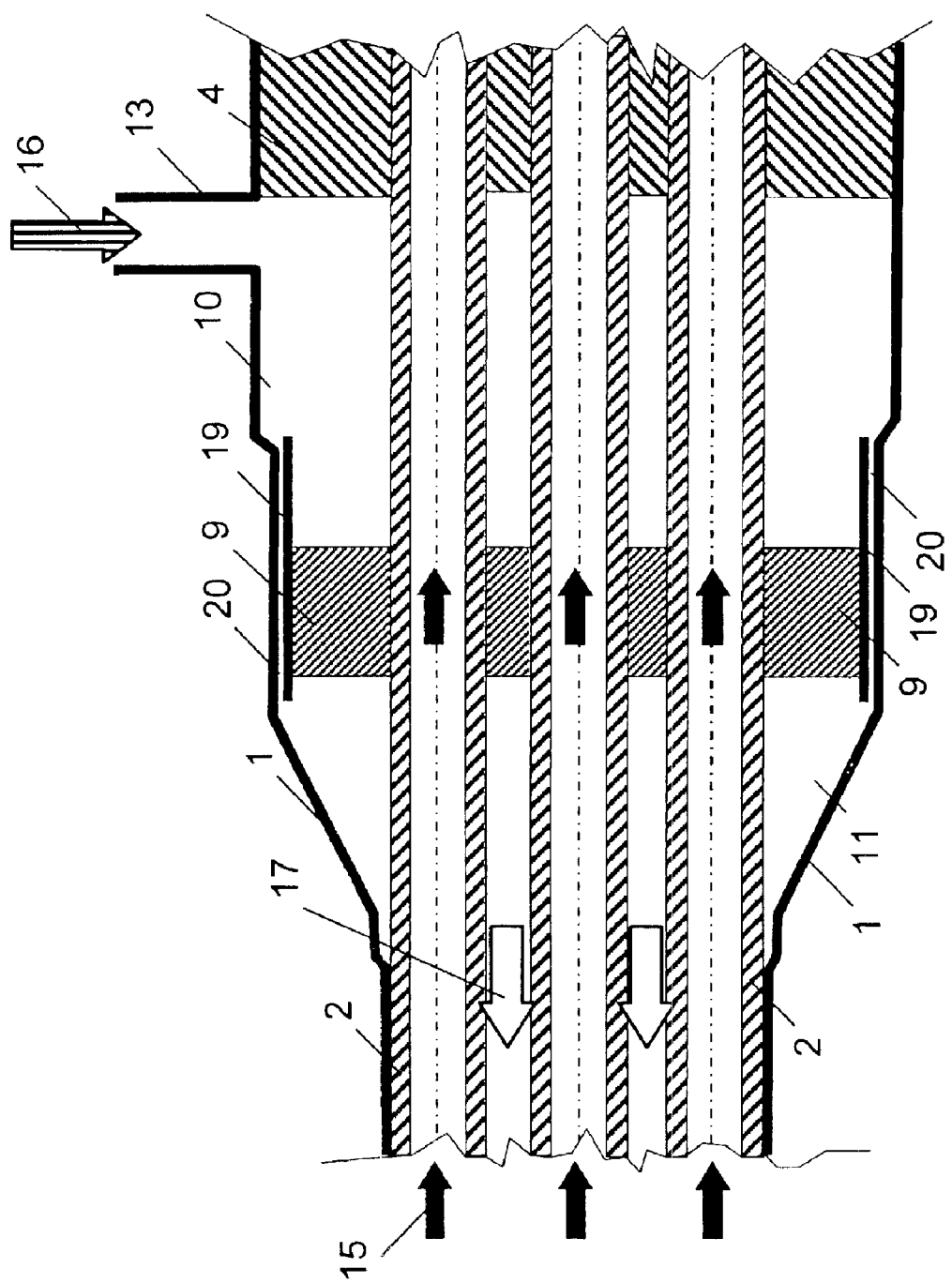
FIG. 3 shows a segment of a longitudinal section through a membrane module of the invention with a dividing wall embedded in a sleeve and a throttle in the form of an annular gap formed between the sleeve and the housing inner wall.

FIG. 3 shows, in an enlarged representation compared to that of FIGS. 1 and 2, a segment of a membrane module of the invention comprising the substituate space 10 and dividing wall 9. The membrane modules and segments thereof as shown in FIG. 3 and the following figures correspond substantially to the membrane module shown in FIG. 1, so that the same components are designated with the same reference numbers and a detailed description is not repeated. FIG. 3 shows an embodiment in which the dividing wall 9 and the bundle of hollow-fiber membranes 2 are embedded in a fluid-tight manner in a dimensionally stable sleeve 19. The sleeve 19 is spaced from the housing inner wall, thus forming an annular gap 20 that constitutes the throttle. The throttle action of the annular gap can be preset in a simple and defined manner by adjusting the width and length of the gap by selection of the sleeve. To stabilize gap 20, spacers can be inserted between sleeve 19 and the inner wall of housing 1. In the membrane module depicted in FIG. 3, the hemodiafiltration includes a post-dilution of the blood with substituate. The blood 15 flows through the hollow-fiber membranes 2 initially in the area of dialyzate space 11 and then in the area of substituate space 10.

Figure 4:
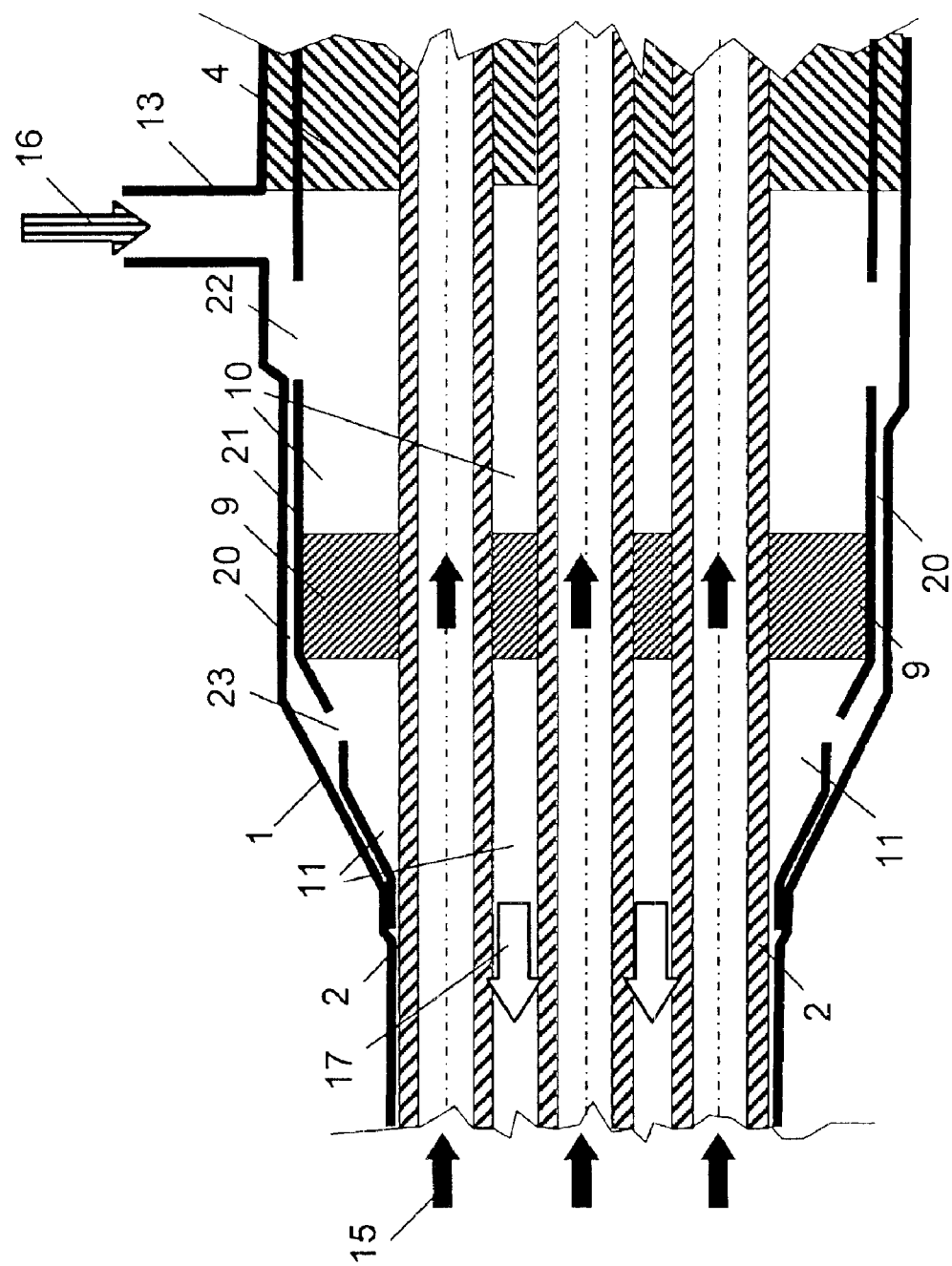
FIG. 4 shows a segment of a longitudinal section through another embodiment of a membrane module of the invention with a dividing wall embedded into a sleeve and a throttle in the form of an annular gap between the sleeve and housing inner wall.

In the segment of a membrane module of the invention as depicted in FIG. 4, an annular gap 20 constituting the throttle is likewise formed between a dimensionally stable sleeve 21 and the inner wall of housing 1. The sleeve, which in this case to simplify manufacture of the membrane module of the invention encloses the entire end of the hollow-fiber membrane bundle facing the substituate space 10, is firmly inserted at its one end into the housing, and the other end is embedded with the hollow-fiber membranes in sealing compound 4. This provides at the same time a stable positioning and formation of the gap 20. By suitably shaping sleeve 21 and housing 1 in the inlet areas of the substituate space 10 and dialyzate space 11, and via openings 22 and 23 in the sleeve, a homogeneous distribution of the substituate and dialyzate 17 over the hollow-fiber membranes is attained. The dialysis liquid 16 is fed to the membrane module via the inlet arrangement 13 and distributes itself uniformly over the periphery in the area of the increased spacing between the sleeve 21 and housing 1. The substituate flows into the substituate space 10 through openings 22 in the sleeve 21. The dialyzate 17 flows via the gap 20 forming the throttle into an area with wider gap between sleeve 21 and the inner wall of housing 1, where the distribution over the periphery is rendered more uniform, before the dialyzate 17 flows into the dialyzate space 11 through openings 23.

Figure 5:
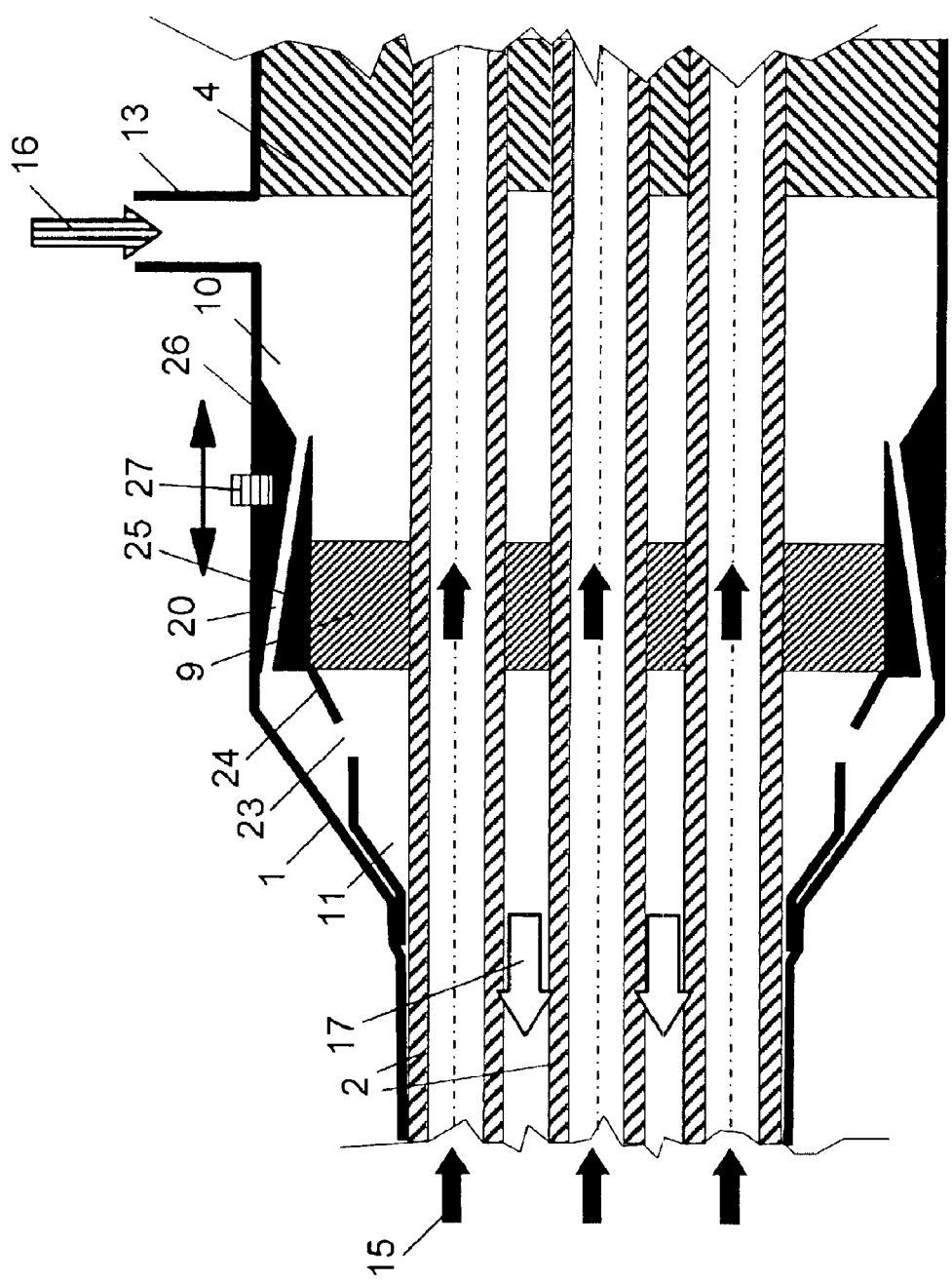
FIG. 5 shows a segment of a longitudinal section through a membrane module of the invention with an adjustable throttle in the form of an annular gap formed by wedges that are displaceable with respect to each other.

FIG. 5 shows another variant of a membrane module of the invention, in which the membrane bundle has been inserted with the dividing wall 9 into a sleeve. The sleeve 24 in the area of dividing wall 9 is shaped as a wedge 25, with the inclined surface facing outward. A wedge 26 is also positioned on the inner wall of housing 1 in this area, the inclined surface of which points inward, and encloses wedge 25 of sleeve 24 in a ring shape. An annular gap 20 is formed between the inclined surfaces of wedges 25,26 and functions as a throttle. In the embodiment depicted in FIG. 5, the width of the annular gap and thus the throttle action can be adjusted by displacing the wedge 26 positioned on the housing wall. As indicated, the wedge 26 can be adjusted from the outside over the longitudinal extent of the housing via an adjusting member 27 passing through the housing wall.

Figure 6:
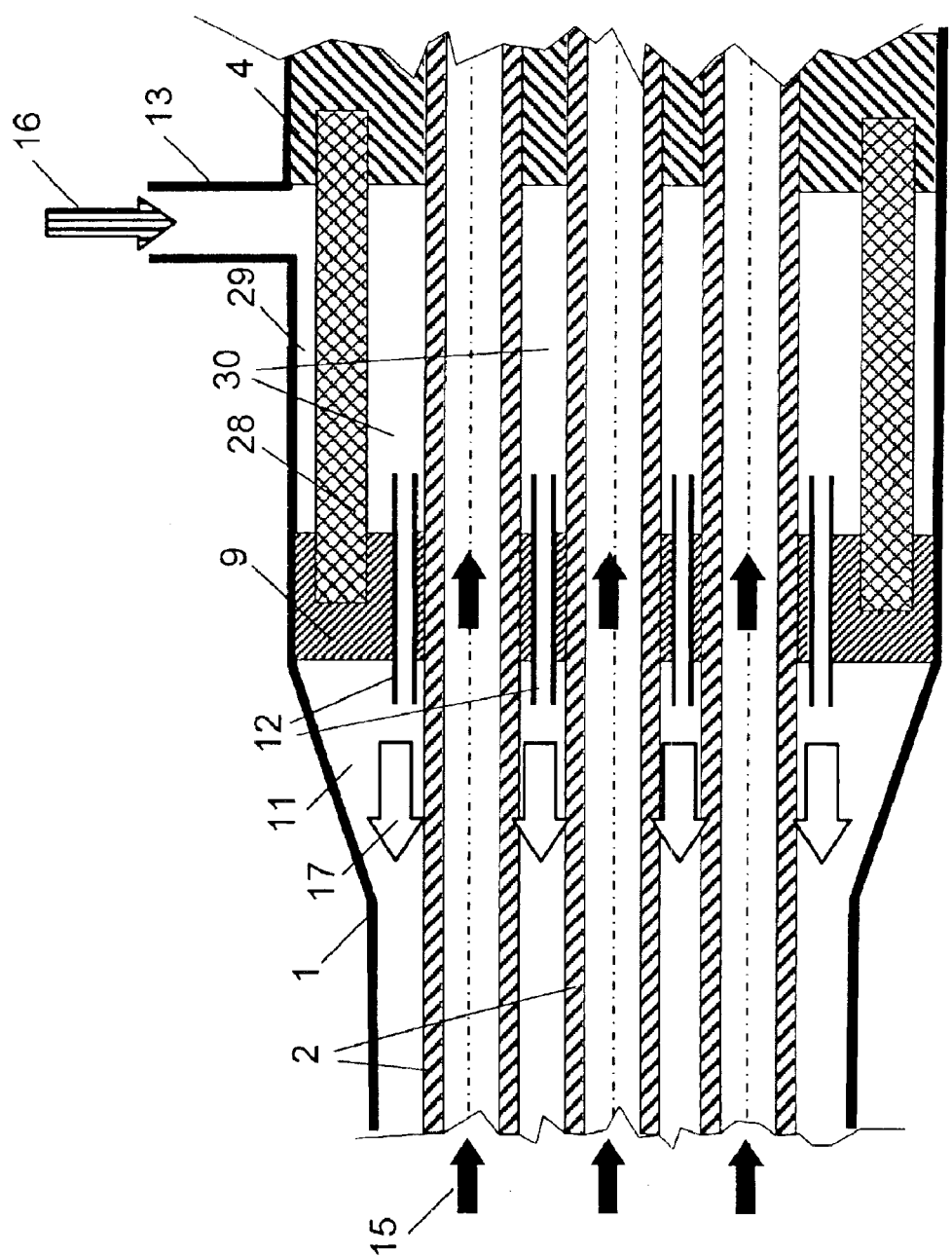
FIG. 6 shows a segment of a longitudinal section through a membrane module of the invention with a sterile filter integrated into the housing and throttles in the form of short capillaries in the area of the inner substituate-space section.

FIG. 6 is a segment of a membrane module of the invention with a sterile filter 28 integrated into housing 1 for sterile filtration of the dialysis liquid 16. The sterile filter 28, preferably in the form of a flat membrane impermeable to bacteria and endotoxins, encloses the hollow-fiber membrane bundle in the substituate space area and divides the substituate space into an outer substituate-space section 29, which is separated from the dialyzate space 11 via the dividing wall 9 in a fluid-tight manner, and an inner substituate-space section 30, which is in fluid communication with dialyzate space 11 via short capillaries 12 functioning as throttles. The sterile filter and hollow-fiber membranes 2 can readily be embedded in the sealing compound 4 and dividing wall 9 in a fluid-tight manner. During use of the embodiment of the hemodiafilter of the invention as shown in FIG. 6, the dialysis liquid introduced into the housing via the inlet arrangement 13 is distributed uniformly in the outer substituate-space section over the entire periphery and flows completely through the sterile filer 28. The dialyzate 17 is introduced into the dialyzate space 11 through the short capillaries 12 distributed over the entire bundle cross-section in the dividing wall 9 in the area of inner substituate-space section 30.

Figure 7:
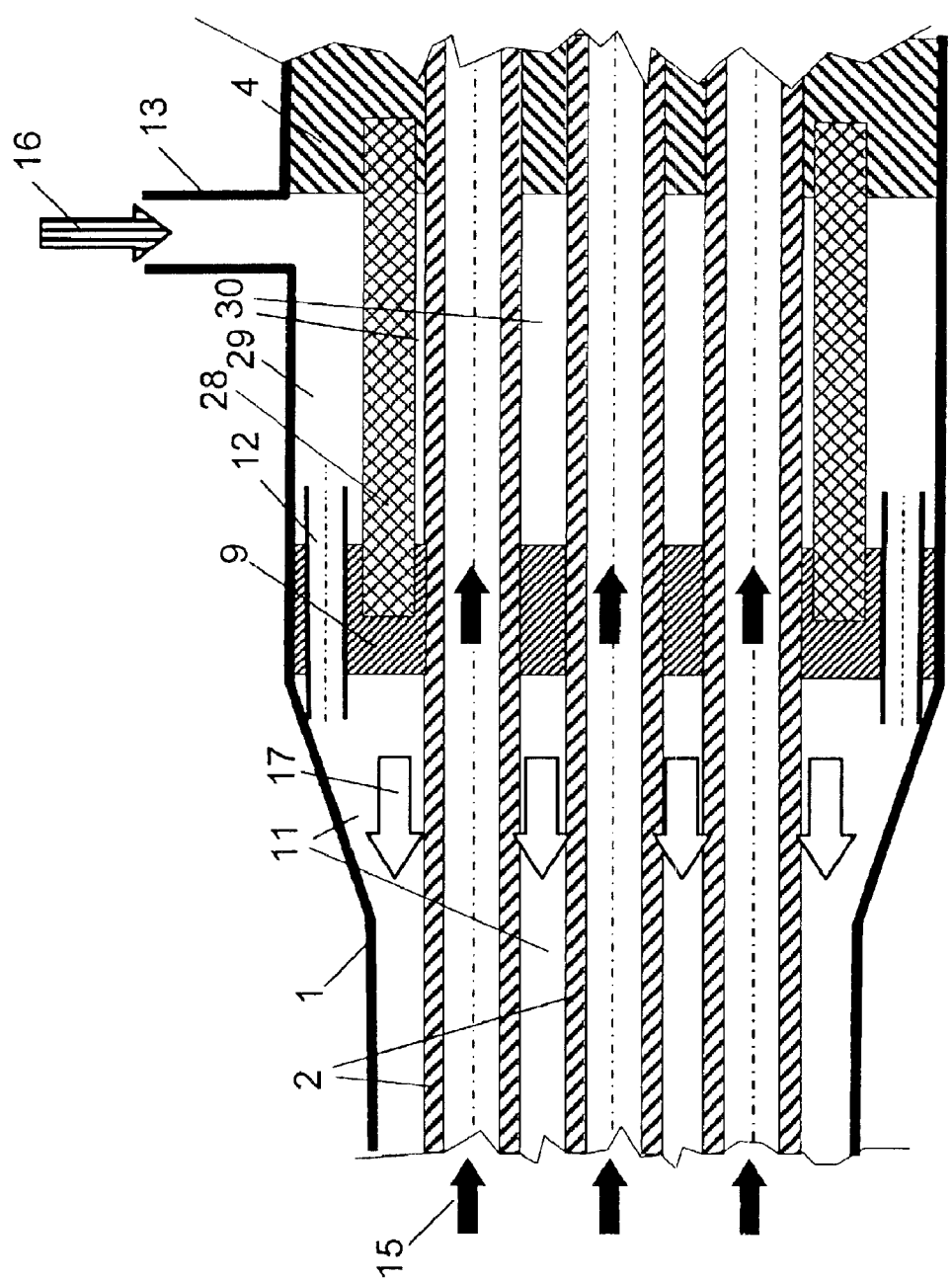
FIG. 7 shows a segment of a longitudinal section through a membrane module of the invention with a sterile filter integrated into the housing and throttles in the form of short capillaries in the area of the outer substituate-space section.

FIG. 7 likewise shows a membrane module of the invention with integrated sterile filter 28, which divides the substituate space into an outer substituate-space section 29 and inner substituate-space section 30. In the module according to FIG. 7, in contrast to the module according to FIG. 6, the short capillaries 12, functioning as throttles, are arranged in the dividing wall in a ring shape around the hollow-fiber membrane bundle such that only the outer substituate-space section 29 is in fluid communication with the dialyzate space 11. The inner substituate-space section 30, on the other hand, is separated from the dialyzate space 11 in a fluid-tight manner. In this embodiment, only the portion of the dialysis liquid 16 that is delivered to the blood as substituate via the walls of hollow-fiber membranes 2 is subjected to sterile filtration. The predominant portion of the dialysis liquid 16 flows as dialyzate 17, which need not meet the stringent purity demands applying to the substituate, without passing through the sterile filter 28, from the outer substituate-space section 29 via the capillaries 12 in the dialyzate space 11.

Figure 8:
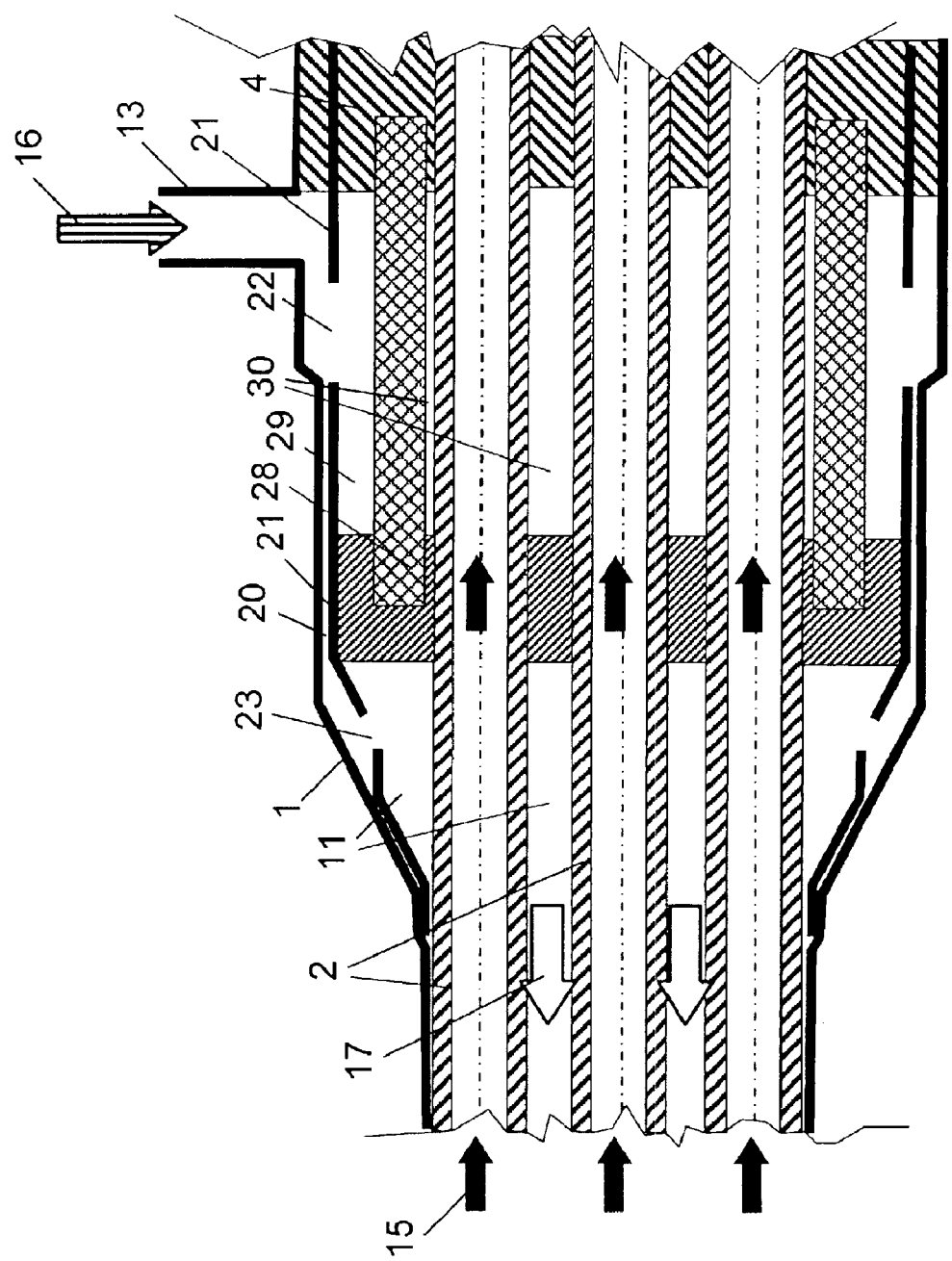
FIG. 8 shows a segment of a longitudinal section through a membrane module of the invention with a sterile filter integrated into the housing and throttles in the form of an annular gap between the sleeve and housing inner wall in the area of the outer substituate-space section.

The membrane module of the invention as depicted in FIG. 8 is similar in construction to that in FIG. 7 and has a sterile filter 28 integrated into the membrane module, the sterile filter 28 dividing the substituate space into an outer substituate-space section 29 and an inner substituate-space section 30, the outer substituate-space section 29 being in fluid communication with the dialyzate space 11. During use of this membrane module, this results in only the portion of the dialysis liquid 16 that is to be delivered to the blood as substituate being filtered by sterile filter 28, whereas the dialyzate portion 17 without this sterile filtration is passed directly into the dialyzate space 11. As in the module depicted in FIG. 4, the throttle is constituted by an annular gap 20, which is formed in the area of dividing wall 9 between a sleeve 21 and the inner wall of housing 1. The sleeve 21 in the embodiment of FIG. 8 corresponds to the one used in the membrane module of FIG. 4, and reference is therefore made to the discussion of FIG. 4 for the characteristics of the sleeve.

Figure 9:
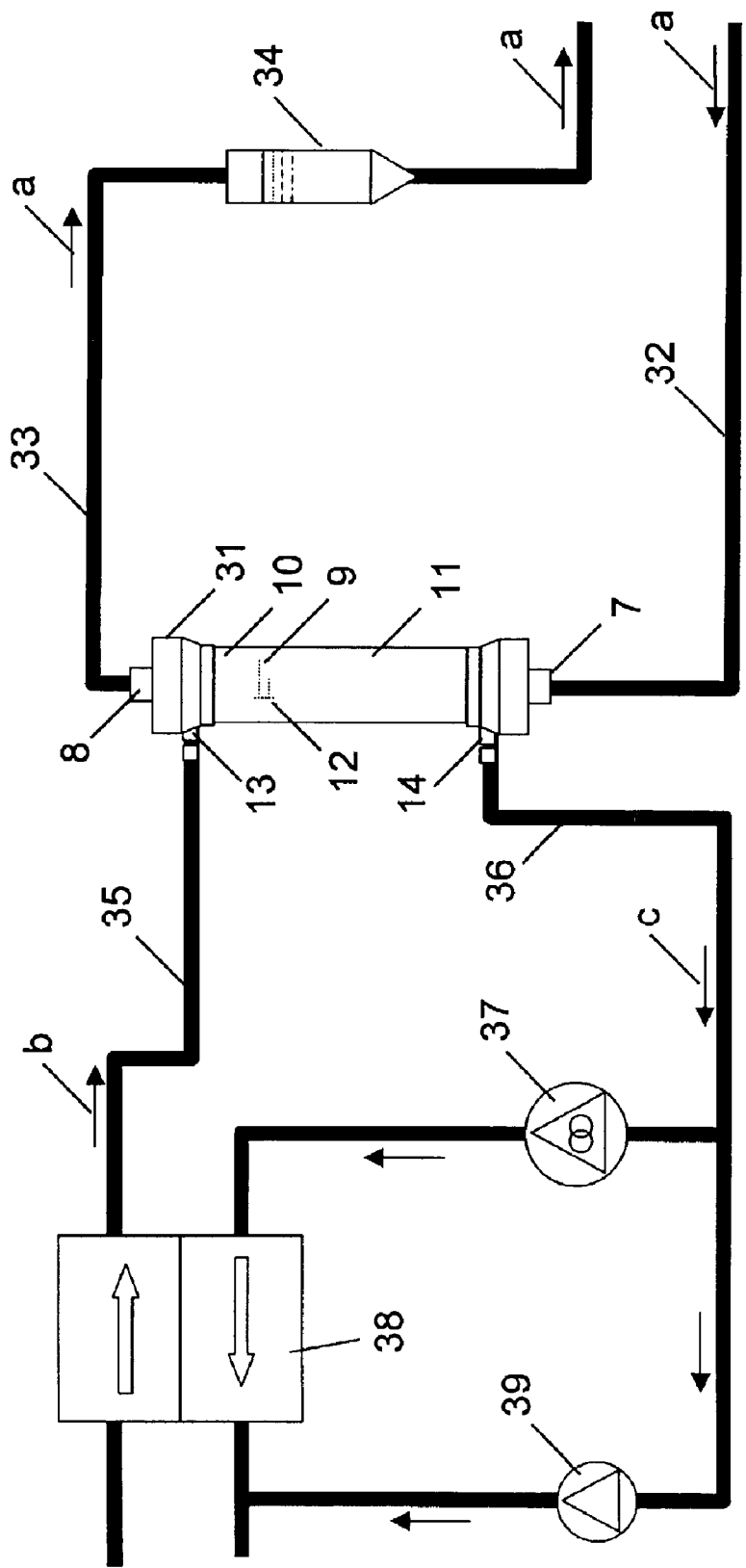
FIG. 9 is a schematic representation of a hemodiafiltration system that uses a membrane module of the invention.

FIG. 9 is a simplified depiction of the basic construction of a hemodiafiltration system in which a membrane module of the invention is used. In the hemodiafiltration system of FIG. 9, which contains the membrane module or hemodiafilter 31 of the invention, the blood taken from the patient is routed in the direction of arrow "a" via a blood supply line 32 to the blood inlet arrangement 7 of the hemodiafilter 31 and through the lumina of the hollow-fiber membranes arranged in the membrane module. The purified blood is withdrawn from the hemodiafilter 31 via its blood outlet arrangement 8, routed in the direction of arrow "a" via the blood withdrawal line 33 into a drip chamber 34 and re-introduced to the patient from that point.

The dialysis liquid is directed in the direction of arrow "b" via the dialysis liquid line 35 and inlet arrangement 13 for the dialysis liquid into the substituate space 10 of the hemodiafilter 31. To increase the pressure, a centrifugal pump can be installed in the dialysis liquid line 35. A portion of the dialysis liquid flows as substituate from the substituate space 10 via the walls of the hollow-fiber membranes arranged in the hemodiafilter 31 into their lumina, where the substituate is mixed with the blood flowing through the lumina. The predominant portion of the dialysis liquid flows as dialyzate into dialyzate space 11 via the throttles arranged in the dividing wall 9, which in this depiction are indicated as short capillaries 12. The dialyzate enriched with the ultrafiltrate withdrawn from the blood leaves the module via the outlet arrangement 14 for the dialyzate and is withdrawn via the dialyzate line 36 in the direction of arrow "c" using dialyzate flow pump 37. The balancing unit 38 provides for controlling the circulation of the dialysis liquid and dialyzate, and the ultrafiltrate pump 39 for adjusting the net filtrate stream withdrawn from the blood in the area of dialyzate space 11. In this case, the balancing unit 38 functions such that the volume stream delivered via the pump 37 is replaced by an identically large volume stream of fresh dialysis liquid.

The hemodiafiltration system according to FIG. 9 has been simplified considerably compared to known hemodiafiltration systems as a result of using the membrane module of the invention. For example, in online hemodiafiltration systems known for example from DE-A 196 07 162, separate devices are always required to remove a portion of the dialysis liquid as a substitute from the supply line for the dialysis liquid and deliver it via a separate supply line to the blood circuit, in which process however the liquid balance of the patient is centrally controlled by a central balancing unit that takes all liquids introduced and withdrawn into account. That is, the substituate is also accounted for by the balancing unit. When using the membrane module of the invention, separate devices such as supply lines or governing apparatus are not needed in the hemodiafiltration system for delivering the substituate to the blood circuit, since the separation of the dialysis liquid into dialyzate and substituate takes place in the membrane module itself via the at least one throttle employed of the invention.

What is claimed is:

1. A membrane module for hemodiafiltration, comprising a cylinder-shaped housing with a longitudinal extent, and in the housing a bundle of hollow-fiber membranes with semipermeable walls and capable of supporting fluid flow through lumina is arranged in a direction of the longitudinal extent of the housing, one end of the hollow-fiber membranes being embedded in a fluid-tight manner in a first sealing compound joined to a housing inner wall in a fluid-tight manner and a second end of the hollow fiber membranes being embedded in a fluid-tight manner in a second sealing compound joined to the housing inner wall in a fluid-tight manner, wherein an exterior space delimited by the first and second sealing compounds and the housing inner wall is formed around the hollow-fiber membranes, the exterior space along the longitudinal extent of the housing being divided into a dialyzate space and a substituate space by a dividing wall comprising a substantially dimensionally stable material, enclosing each of the hollow-fiber membranes, and arranged substantially transversely to the hollow-fiber membranes, the dialyzate space and substituate space each having at least one opening for introducing or draining a fluid, wherein at least one throttle is arranged in the exterior space by which the dialyzate space and substituate space are in fluid communication with each other.

2. The membrane module according to claim 1, wherein the dividing wall is joined to the housing inner wall in a fluid-tight manner and the at least one throttle is integrated into the dividing wall.

3. The membrane module according to claim 2, wherein the at least one throttle integrated into the dividing wall is at least one capillary, via the lumen, of which the dialyzate space and substituate space are in fluid communication with each other.

4. The membrane module according to claim 3, wherein the at least one capillary extends through the dialyzate space and terminates in the area of the second sealing compound delimiting the dialyzate space, and the opening of the dialyzate space is adjacent to the dividing wall.

5. The membrane module according to claim 3, wherein a plurality of capillaries are inserted into the dividing wall, the capillaries being arranged around the bundle of hollow-fiber membranes.

6. The membrane module according to claim 3, wherein a single capillary extending through the dialyzate space is inserted into the dividing wall, the capillary being centrally arranged in the bundle of hollow-fiber membranes.

7. The membrane module according to claim 1, wherein the at least one throttle is an annular gap that is formed between the dividing wall and the housing inner wall.

8. The membrane module according to claim 1, wherein the dividing wall is embedded in a sleeve and the at least one throttle is an annular gap that is formed between an outside of the sleeve and the housing inner wall.

9. The membrane module according to claim 1, wherein a plurality of throttles are arranged in a form of annular-gap segments in the dividing wall around the bundle of hollow-fiber membranes or along a periphery of the dividing wall.

10. The membrane module according to claim 1, wherein the at least one throttle is adjustable.

11. The membrane module according to claim 1, wherein viewed in a direction of the longitudinal extent of the cylinder-shaped housing, a ratio $L_d/L_s$, wherein $L_d$ is the length of the dialyzate space and $L_s$ is the length of the substituate space, is between 3 and 20.

12. The membrane module according to claim 11, wherein the ratio is between 5 and 15.

13. The membrane module according to claim 1, wherein the dividing wall consists of a sealing compound.

14. The membrane module according to claim 13, wherein the dividing wall and the first and second sealing compounds are made of the same material.

15. The membrane module according to claim 1, wherein the dividing wall has a thickness between 1 and 15 mm.

16. The membrane module according to claim 1, wherein an inside of the cylinder-shaped housing in the area of the dialyzate space tightly encloses the bundle of hollow-fiber membranes, and the cylinder-shaped housing exhibits an expanded cross-section in an area of the dividing wall and the substituate space.

17. The membrane module according to claim 1, wherein in an area of the substituate space, a sterile filter is arranged around and encloses the bundle of hollow-fiber membranes.

18. The membrane module according to claim 17, wherein the sterile filter is a microporous flat membrane.

19. The membrane module according to claim 1, wherein the hollow-fiber membranes have an ultrafiltration rate for water of from 20 to 1500 ml/(h·m²·mmHg).

20. The membrane module according to claim 1, wherein the hollow-fiber membranes are impermeable to endotoxins.

21. A process of hemodiafiltration comprising:

introducing blood into a blood inlet at one end of the membrane module of claim 1, so that the blood flows through the lumina of the hollow-fiber membranes;

introducing a dialysis liquid into the substituate space;

delivering a portion of the dialysis liquid as a substitute to the blood flowing through the lumina of the hollow-fiber membranes via the walls of the portions of the hollow-fiber membranes located in the substituate space, wherein a majority of the dialysis liquid is directed by the at least one throttle as dialyzate from the substituate space into and flows through the dialyzate space, thereby taking up in the dialyzate space an ultrafiltrate withdrawn from the blood via ultrafiltration through the walls of the hollow fiber membranes, so that the substances normally eliminated in the urine are removed from the blood;

withdrawing the dialyzate mixed with the ultrafiltrate from the dialyzate space; and recovering the blood from a blood outlet at an opposite end of the membrane module.

* * * * *

UNITED STATES PATENT AND TRADEMARK OFFICE
CERTIFICATE OF CORRECTION

PATENT NO. : 6,918,886 B1
DATED : July 19, 2005
INVENTOR(S) : Ulrich Baurmeister It is certified that error appears in the above-identified patent and that said Letters Patent is hereby corrected as shown below:

Column 8,
Line 4, insert -- . -- after "area".

Column 12,
Lines 42 and 60, change "scaling" to -- sealing --.

Column 13,
Line 7, change "area," to -- area. --.
Lines 13 and 17, change "scaling" to -- sealing --.

Signed and Sealed this

Fourth Day of October, 2005

JON W. DUDAS
*Director of the United States Patent and Trademark Office*